United States Patent
Luo et al.

(10) Patent No.: US 9,833,490 B1
(45) Date of Patent: Dec. 5, 2017

(54) DRUG COMBINATION FOR THE TREATMENT OF INFERTILITY AND ITS PREPARATION METHODS AND APPLICATIONS

(71) Applicant: SICHUAN SHANZE BIOTECH.,LTD., Sichuan (CN)

(72) Inventors: Mingfeng Luo, Sichuan (CN); Xiaoxue Guo, Sichuan (CN); Gaili Li, Sichuan (CN)

(73) Assignee: SICHUAN SHANZE BIOTECH., LTD., Sichuan (CN)

( * ) Notice: Subject to any disclaimer, the term of this patent is extended or adjusted under 35 U.S.C. 154(b) by 0 days.

(21) Appl. No.: 15/452,255

(22) Filed: Mar. 7, 2017

(51) Int. Cl.
| | |
|---|---|
| A61K 36/8945 | (2006.01) |
| A61K 36/185 | (2006.01) |
| A61K 36/64 | (2006.01) |
| A61K 36/65 | (2006.01) |
| A61K 36/40 | (2006.01) |
| A61K 36/076 | (2006.01) |
| A61K 36/481 | (2006.01) |
| A61K 36/344 | (2006.01) |
| A61K 36/71 | (2006.01) |
| A61K 36/725 | (2006.01) |
| A61K 31/592 | (2006.01) |
| A61K 36/48 | (2006.01) |

(52) U.S. Cl.
CPC ........ *A61K 36/8945* (2013.01); *A61K 31/592* (2013.01); *A61K 36/076* (2013.01); *A61K 36/185* (2013.01); *A61K 36/344* (2013.01); *A61K 36/40* (2013.01); *A61K 36/48* (2013.01); *A61K 36/481* (2013.01); *A61K 36/64* (2013.01); *A61K 36/65* (2013.01); *A61K 36/71* (2013.01); *A61K 36/725* (2013.01); *A61K 2236/15* (2013.01)

(58) Field of Classification Search
None
See application file for complete search history.

(56) References Cited

FOREIGN PATENT DOCUMENTS

WO   WO 2008/119131 A1 * 10/2008

* cited by examiner

*Primary Examiner* — Susan Hoffman
(74) *Attorney, Agent, or Firm* — WPAT, P.C., Intellectual Property Attorneys; Anthony King

(57) ABSTRACT

The present invention provides a drug combination for the treatment of infertility and its crude drug comprises the medical ingredients with their weight proportions listed as below: 10-20 amounts by weight of Rehmannia, 10-20 amounts by weight of Chinese Peony, 10-20 amounts by weight of Asiatic Dogwood, 10-20 amounts by weight of Chinese Yam, 10-20 amounts by weight of Poria, 15-25 amounts by weight of *Astragalus*, 15-25 amounts by weight of Codonopsis, 10-20 amounts by weight of Epimedium and 10-20 amounts by weight of Jujube. The compatibility of this drug combination invented is precise, appropriate and possess outstanding curative effects. As shown in many experiments, the drug combination invented is safe and reliable, its toxic & side-effect is low and it has obvious improvement effects on female infertility caused by androgen, fallopian tube inflammation, tubal blockage and other factors. Furthermore, it can not only significantly improve the success rate of pregnancy, but also improve immunity and enhance the body's anti-fatigue and hypoxia tolerance. In short, the invention provides a safe and reliable new choice for clinical medication.

1 Claim, No Drawings

DRUG COMBINATION FOR THE TREATMENT OF INFERTILITY AND ITS PREPARATION METHODS AND APPLICATIONS

FIELD OF THE DISCLOSURE

This invention relates to a drug combination for the treatment of infertility and its preparative method and applications.

BACKGROUND OF THE DISCLOSURE

In recent years, due to impacts of psychological, environmental, social and other factors, the fertilities of couples of child-bearing ages throughout the world have presented declining trend year by year and most of the reasons are caused by the decline of female fertility. Female infertility is mainly attributable to the following reasons:

1. Long-term endocrine disorders. Female endocrine disorders often manifested by amenorrhea, dysmenorrhea, low estrogen, menstrual cycle disorder, ovulatory bleeding, metabolic disorders and other symptoms. Behind this series of symptoms, there are hidden ovulation disorders, polycystic ovary syndrome, HPRL, corpus *luteum* insufficiency, ovarian insufficiency, premature ovarian failure and other diseases which serve as important factors that lead to infertility;

2. Long-term suffering from gynecological, inflammations that mainly comprise vaginitis, cervicitis, PID (pelvic inflammatory disease) and adnexitis, etc. Among the rest, PID is mainly manifested by bilateral salpingitis that causes obstruction in ovum, sperm or fertilized egg and thus leads to infertility. Severe PID may spread to tissues beside pelvic peritoneum, womb and uterine cervix, causing these organs to lose physiological properties of soft peristalsis and the lumen to be completely blocked and incapable of getting pregnant;

3. Repeated improper abortion. Those women who have repeated improper abortions are high risk population of infertility. Improper abortion can easily cause postoperative infection, fallopian tube inflammation, severe endometrial impairment and other circumstances. Ultimately, it may cause these women to find it extremely difficult to get pregnant or such serious consequences as habitual abortion or threatened abortion may appear after pregnancy.

The clinical treatment of female infertility is relatively tricky and western medicine is dominated in the current treatment in terms of generally supplementing estrogenic drugs or operative therapy. Despite of some certain effects, this treatment is featured with great damage to body and more obvious toxic and side-effects.

BRIEF SUMMARY OF THE DISCLOSURE

The aims of present invention lie in two, one is to provide a kind of drug combination for the treatment of infertility and the other is to provide its preparative method and applications.

This invention provides a drug combination for the treatment of infertility and its crude drug comprises the medical ingredients with their weight proportions listed as below:

10-20 amounts by weight of Rehmannia, 10-20 amounts by weight of Chinese Peony, 10-20 amounts by weight of Asiatic Dogwood, 10-20 amounts by weight of Chinese Yam, 10-20 amounts by weight of Poria, 15-25 amounts by weight of *Astragalus*, 15-25 amounts by weight of Codonopsis, 10-20 amounts by weight of Epimedium and 10-20 amounts by weight of Jujube.

The sterility as mentioned in this invention refers to female infertility.

Furthermore, its crude drug comprises the medical ingredients with their weight proportions listed as below:

15 amounts by weight of Rehmannia, 15 amounts by weight of Chinese Peony, 15 amounts by weight of Asiatic Dogwood, 15 amounts by weight of Chinese Yam, 15 amounts by weight of Poria, 20 amounts by weight of *Astragalus*, 20 amounts by weight of Codonopsis, 15 amounts by weight of Epimedium and 15 amounts by weight of Jujube.

Furthermore, its crude drug comprises the medical ingredients with their weight proportions listed as below:

10-20 amounts by weight of Rehmannia, 10-20 amounts by weight of Chinese Peony, 10-20 amounts by weight of Asiatic Dogwood, 10-20 amounts by weight of Chinese Yam, 10-20 amounts by weight of Poria, 15-25 amounts by weight of *Astragalus*, 15-25 amounts by weight of Codonopsis, 10-20 amounts by weight of Epimedium and 10-20 amounts by weight of Jujube.

Preferably, its crude drug comprises the medical ingredients with their weight proportions listed as below:

15 amounts by weight of Rehmannia, 15 amounts by weight of Chinese Peony, 15 amounts by weight of Asiatic Dogwood, 15 amounts by weight of Chinese Yam, 15 amounts by weight of Poria, 20 amounts by weight of *Astragalus*, 20 amounts by weight of Codonopsis, 15 amounts by weight of Epimedium and 15 amounts by weight of Jujube.

Among the rest, it is the dosage form prepared by use of the powder drug from crude drug or water or/and ethanol extract (active component) of the crude drug plus excipients or accessory components commonly used in pharmacy.

Water extract or powder medicine belong to traditional methods of administration in traditional Chinese medicine. After the water extraction, as the dissolved water range is wide and able to dissolve out the most effective components and make the drug more easily absorbed by human body and achieve faster onset. For example, the decoction and other forms of medication. Using the raw powder into medicine can leave larger surface area and facilitate the absorption of effective constituents in the medicinal material. However, as the medicinal material remains unextracted and effective constituents still require to be dissolved inside the body for reabsorption, its onset is slower than that of water extract, the toxic and side effects caused by harmful ingredients in the medicinal material can be weakened and suitable for long-term dosing. For example, the original powder can be prepared into pills and other forms of medication. At present, during the pharmaceutical manufacturiong process, ethanol is taken as solvent for the extraction of drugs, which is also one of the most commonly-used extractions. As a semi-polar solvent, its solubility property falls between the polar solvent and nonpolar solvent. Therefore, it can only dissolve some water soluble constituents, but also dissolve some constituents dissolved in non-polar solvents. Normally, ethanol is used to replace the water decoction and thus avoid the dissolution of a large number of ineffective ingredients and improve the concentration of effective components and extraction efficiency. However, as price of ethanol is expensive if compared with water, water decoction is usually dominated in the mass production of modern pharmaceutical industry, so as to save the cost of production. Under the premise that the alcohol extract of drug combination possesses the physiological activity in this invention, it is feasible to prepare the specific dosage forms by arbitrarily choose the water extraction, raw powder, alcohol extraction or their combination methods, so as to be fit for various demands for production and uses.

The pharmaceutically-acceptable auxiliary materials as mentioned in this invention shall include but not limited to the filling agent (diluent), lubricant (glidant or antiadherent), dispersant, wetting agent, binding agent, moderator, solubilizer, antioxidant, antibacterial agent, emulsifier, disintegrant, etc. The binding agent contains syrup, arabic gum, gelatin, sorbitol, gum tragacanth, cellulose and its derivatives (e.g., microcrystalline cellulose, sodium methyl cellulose, ethyl cellulose or light propyl methyl cellulose, etc.), gelatin mucilage, syrup, starch slurry or polyvinylpyrrolidone(PVP), etc. The filler contains lactose, powdered sugar, dextrin, starch and its derivatives, cellulose and its derivatives, inorganic calcium salt (e.g. calcium sulfate, calcium phosphate, calcium phosphate, calcium carbonate sedimentation and so on), sorbitol or glycine, etc. The lubricant contains micropowder silica gel, magnesium stearate, talcum powder, aluminum hydroxide, boric acid, hydrogenated vegetable oil, polyethylene glycol, etc. The disintegrant contains starch and its derivatives (e.g. carboxymethyl starch sodium, sodium starch glycolate, pregelatinized starch, modified starch, hydroxypropyl corn starch, corn starch and so on), polyvinylpyrrolidone or microcrystalline cellulose, etc. The wetting agent contains sodium dodecyl sulfate, water or alcohol, etc. The antioxidant contains sodium sulfite, sodium bisulfite, sodium metabisulfite, dibutyl benzoic acid, etc. The antibacterial agent contains 0.5% of phenol, 0.3% of cresol and 0.5% of chlorbutanol. The moderator contains hydrochloric acid, citric acid, potassium hydrate (sodium hydroxide), sodium citrate and buffer (including sodium dihydrogen phosphate and disodium hydrogen phosphate), etc. The emulsifier contains polysorbate-80, sorbitan, pluronic-68, lecithin, soy lecithin, etc. The solubilizer contains tween-80, bile, glycerin, etc.

The said pharmaceutically-acceptable auxiliary components possess a certain physiological activity, but the addition of these components will not change the dominant role of above-mentioned drug combination in the process of disease treatment. Instead, it only play auxiliary effects that utilize the known activity. In short, it serves as a complementary therapeutic modality in the field of medicine.

Wherein, the said dosage form is the dosage form administered via gastrointestinal tract. For example, tablet, pill, powder, capsule, granule or oral liquid.

This invention also provides the method for preparation of above-mentioned drug combination, including the following procedures:

(1) Weighing and taking the crude drug as per the proportion;

(2) Adding water the extract the crude drug. For aqueous extracts, it is required to add pharmaceutically-acceptable excipients or accessory components according to the conventional preparation technology, so as to prepare pharmaceutically-acceptable dosage forms.

The water-added extraction as mentioned in this invention includes the water decoction, warm immersion, ultrasonic, extraction at normal or reduced pressure and other various extraction modes. The same or similar extraction effects can be realized as long as the water is taken as dissolvant and supplemented by conventional detection means.

Furthermore, the specific operation of water-added extraction as mentioned in the procedure (2) can be described like this, carrying out the water decoction for 2-4 times, adding the water equivalent to 4-6 times of the drug weight and decocting for 1-3 hours every time.

The invention also provides the applications of the above-mentioned drug combination used for the treatment of infertility, immunity improvement and fatigue resistance or hypoxic tolerance.

Furthermore, the said drug for infertility treatment is used to treat the infertility caused by androgen or fallopian tube inflammatory obstructive infertility.

Furthermore, the said drug for the treatment of infertility caused by androgen can improve the estrogen level, increase follicle, oocyte and interstitial gland composition. The said drug for the treatment of fallopian tube inflammatory obstructive infertility can improve the fallopian tube obstruction symptom and reduce the blood viscosity.

In this invention, Rehmannia, Chinese Peony, Asiatic Dogwood, Chinese Yam, Poria, *Astragalus*, Codonopsis, Epimedium and Jujube are used for women to recuperate the vitality and play the roles of improving abnormal leucorrhea, irregular menstruation, trance, anemia, pregnancy rate and treating infertility. Among the rest, Rehmannia and Epimedium possess the efficacy of nourishing blood and regulating menstruation. Asiatic Dogwood is conducive to improving the efficacy of Rehmannia Chinese Peony can improve the sweating symptoms. Chinese Yam can be used to improve the abnormal leukorrhea. *Astragalus* and Codonopsis can be used to nourish blood, improve appetite and enhance physical power. Jujube and Poria possess the efficacy of benefiting qi and nourishing blood, improving distrait and disturbed sleep.

The compatibility of this drug combination invented is precise, appropriate and possess outstanding curative effects. As shown in many experiments, the drug combination invented is safe and reliable, its toxic & side-effect is low and it has obvious improvement effects on female infertility caused by androgen, fallopian tube inflammation, tubal blockage and other factors. Furthermore, it can not only significantly improve the success rate of pregnancy, but also improve immunity and enhance the body's anti-fatigue and hypoxia tolerance. In short, the invention provides a safe and reliable new choice for clinical medication.

Apparently, a variety of other forms of modifications, replacements or changes may also be made available according to the above-mentioned contents of present invention and based on the normal technical knowledge and means in this field, under the premise of not deviating the above basic technical concept of present invention.

Further detailed description is given to the above-mentioned contents of present invention through the form of specific embodiments. However, it should not be interpreted as that the scope of above theme is only limited to the following embodiments. All technologies realized by basing upon the above contents of present invention shall belong to the scope of present invention.

DETAILED DESCRIPTION OF THE EMBODIMENTS

Embodiment 1: Preparative Method for the Drug Combination of Present Invention

Presciption:

15 kg of Rehmannia, 15 kg of Chinese Peony, 15 kg of Asiatic Dogwood, 15 kg of Chinese Yam, 15 kg of Poria, 20 kg of *Astragalus,* 20 kg of Codonopsis, 15 kg of Epimedium and 15 kg of Jujube.

Preparative Method:

Respectively taking all kinds of crude drugs, adding water independently and decocting for three times. For the first time, it is required to add the water equivalent to 6 times of the crude drug weight, soak for 1 hour and then decocted for 2 hours. For the second time, it is required to add the water equivalent to 5 times of the crude drug weight, soak for 1 hour. For the third time, it is required to add the water equivalent to 4 times of the crude drug weight, decocted for 1 hour, filter out, combine the filtrate, heat and concentrate until the relative density has reached 1.09-1.12 under 60-65° C. Finally, it is required to carry out spray dehydration of above concentrated solution by use of high speed centrifugal spray dryer and prepare into dry extract powders of various crude drugs (80-120 meshes).

Mixing all kinds of dry extract powders, adding appropriate amount of fillers and prepare drug granules.

Embodiment 2: Preparative Method for the Drug Combination of Present Invention

Presciption:

15 kg of Rehmannia, 15 kg of Chinese Peony, 15 kg of Asiatic Dogwood, 15 kg of Chinese Yam, 15 kg of Poria, 20 kg of *Astragalus*, 20 kg of Codonopsis, 15 kg of Epimedium and 15 kg of Jujube, 75 kg of Paricalcitol, and 60 kg of *Acacia* extracts. Preparative method:

*Nelumbo nucifera* leaves were harvested from field and the leaves were cleaned with water and air-dried. 80 g dried leaves were cut into small pieces and extracted with 500 ml distilled water in 4° C. in a period of 12 hours. The extract was filtered through a Whatman paper No. 1, and concentrated by evaporation, and lyophilized to yield *Nelumbo* leaf extract (NLE). Respectively taking all kinds of crude drugs, adding water and decocting for three times after the mixing. For the first time, it is required to add the NLE to 6 times of the crude drug weight, soak for 1 hour and then decocted for 2 hours. For the second time, it is required to add the NLE to 5 times of the crude drug weight and decocted for 1 hour. For the third time, it is required to add the NLE to 7 times of the crude drug weight, decocted for 1 hour, filter out, combine the filtrate, heat and concentrate until the relative density has reached 1.09-1.12 under 60-65° C. Finally, it is required to carry out spray dehydration of above concentrated solution by use of high speed centrifugal spray dryer and prepare into dry extract powders of various crude drugs (80-120 meshes). Mixing all kinds of dry extract powders, adding appropriate amount of fillers and prepare capsules.

The crude drugs can consists of 15 kg of Rehmannia, 15 kg of Chinese Peony, 15 kg of Asiatic Dogwood, 15 kg of Chinese Yam, 15 kg of Poria, 20 kg of *Astragalus*, 20 kg of Codonopsis, 15 kg of Epimedium and 15 kg of Jujube, 75 kg of Paricalcitol, and 60 kg of *Acacia* extracts.

The *Acacia* extracts of the present invention are extracted from *Acacia* heartwood, bark, branches, flowers, twigs, roots and leaves. Extracts with preferred xanthine oxidase inhibitory activity is extracted from heartwood, and the second preferred one is extracted from bark. The *Acacia* extract by organic solvent, such as ethanol, of the present invention is further separated in liquid-liquid fraction with ethyl acetate, n-butyl alcohol and water to generate ethyl acetate fraction, n-butyl alcohol fraction and water fraction. The ethyl acetate fraction with better xanthine oxidase inhibitory activity can isolate eight major compounds, including 3,7,8,3',4'-pentahydroxyflavone (Melanoxetin), 7,8,3',4'-tetrahydroxyflavon, 3,4,2',3',4'-pentahydroxy trans-chalcone (Okanin), 7,8,3',4'-tetrahydroxy-3-methoxyflavone (Transilitin), 3,7,8,3'-tetrahydroxy-4'-methoxyflavone, 7,8,3'-trihydroxy-3,4'-dimethoxyflavone, 7,3',4'-trihydroxyflavone and 7,3',4'-trihydroxy-3-methoxyflavone, wherein the substances with better xanthine oxidase inhibitory activity are melanoxetin and okanin, and the best one is okanin. The xanthine oxidase inhibitory activity of melanoxetin and okanin is 17 fold and 63 fold higher than current gout treating drug allopurinol. Therefore, they are potential substitutes for allopurinol which has side effect. The *Acacia* of the present invention includes but is not limited to *Acacia acinacea*, *Acacia albida*, *Acacia aneura*, *Acacia Arabica*, *Acacia auriculiformis*, *Acacia baileyana*, *Acacia baileyana*, *Acacia bealbat*, *Acacia binervia*, *Acacia brachybotrya*, *Acacia bussei*, *Acacia bynoeana*, *Acacia caesia*, *Acacia calamifolia*, *Acacia cardiophylla*, *Acacia catechu*, *Acacia cavenia*, *Acacia concinna*, *Acacia confusa*, *Acacia cornigera*, *Acacia cultriformis*, *Acacia cultriformis*, *Acacia cyanophylla*, *Acacia cyclopis*, *Acacia dealbara*, *Acacia decora*, *Acacia decurrens*, *Acacia elongate*, *Acacia falcate*, *Acacia famesiana*, *Acacia fimbriate*, *Acacia giraffae*, *Acacia gregii*, *Acacia gummifera*, *Acacia holosericea*, *Acacia homalophylla*, *Acacia horrida*, *Acacia howittii*, *Acacia implexa*, *Acacia juniperina*, *Acacia karroo*, *Acacia kettlewelliae*, *Acacia koa*, *Acacia lenticularis*, *Acacia leprosa*, *Acacia leucophloea*, *Acacia longifolia*, *Acacia mangium*, *Acacia mearnsii*, *Acacia melanoxylon*, *Acacia mellifera*, *Acacia merrillii*, *Acacia mollissima*, *Acacia nigrescens*, *Acacia nilotica*, *Acacia paniculata*, *Acacia paradoxa*, *Acacia pendula*, *Acacia pennata*, *Acacia penninervis*, *Acacia podalyriifolia*, *Acacia pravissima*, *Acacia prominens*, *Acacia pruinosa*, *Acacia pubescens*, *Acacia pycnantha*, *Acacia retinodes*, *Acacia richii*, *Acacia rigens*, *Acacia rubida*, *Acacia salicina*, *Acacia Senegal*, *Acacia seyal*, *Acacia sinuate*, *Acacia spectabilis*, *Acacia spirocarpa*, *Acacia suaveolens*, *Acacia terminalis*, *Acacia vestita*, *Acacia victoriae*, *Acacia woodii*, wherein the preferable *Acacia* is *Acacia melanoxylon*, *Acacia nigrescens* or *Acacia confusa*, and the most preferred is *Acacia confusa*.

Embodiment 3: Preparative Method for the Drug Combination of Present Invention

Presciption:

20 kg of Rehmannia, 10 kg of Chinese Peony, 10 kg of Asiatic Dogwood, 10 kg of Chinese Yam, 10 kg of Poria, 15 kg of *Astragalus*, 15 kg of Codonopsis, 10 kg of Epimedium and 10 kg of Jujube.

Preparative Method:

Taking various crude drugs, carrying out the ethanol soakage extraction with 55-65% v/v ethanol after mixing. After recycling the ethanol with extracting solution, it is required to concentrate, add appropriate amount of excipients and prepare tablets.

Embodiment 4: Preparative Method for the Drug Combination of Present Invention

Presciption:

10 kg of Rehmannia, 20 kg of Chinese Peony, 20 kg of Asiatic Dogwood, 20 kg of Chinese Yam, 20 kg of Poria, 25 kg of *Astragalus*, 25 kg of Codonopsis, 20 kg of Epimedium and 20 kg of Jujube, 75 kg of Paricalcitol. Paricalcitol is a vitamin $D_2$ derived sterol lacking the carbon-19 methylene group found in all natural vitamin D metabolites. A novel class of vitamin D-related compounds, namely the 1α-hydroxy-19-nor-vitamin D analogs, as well as a general method for their chemical synthesis are disclosed in U.S. Pat. No. 5,710,294 and U.S. Pat. No. 5,342,975. Furthermore, U.S. Pat. No. 6,359,012 provides the method for making 24(s)-hydroxyvitamin $D_2$, which is the first sterospecific synthesis of 24(s)-hydroxyvitamin $D_2$ by coupling of (S)-(+)-2,3-dimethyl-2-triethylsilyloxybutyraldehyde and a vitamin D phosphine oxide derivative to form a C-3 and C-24 diprotected trans-vitamin $D_2$ which is then deprotected and irradiated to yield the 24(S)-hydroxyvitamin $D_2$.

Preparative Method:

Taking various crude drugs and carrying out the ethanol reflux extraction with 80-95% v/v ethanol after mixing. After recycling the ethanol with extracting solution, it is required to leave the concentrated solution for stand-by application. Adding water to gruffs and decocting for 2 times, the amount of water addition shall be 6-10 times equivalent to the crude drug weight at each time and it is required to decocted for 1 hour, collect the water decoction, merge with the concentrated solution for condensation and drying and add appropriate amount of excipients and prepare pills.

The following testing examples are used to specify the beneficial effects of present invention. The drug combination obtained from the above embodiment 1 of present invention is taken as the test drug to conduct the following experimental investigations, which can manifest the remarkable effects of this drug combination.

Among all testing drugs, the dosage shall be calculated as per the crude drug weight (g/kg) equivalent to the corresponding raw material extracted.

Testing Example 1: Effects on Infertility (1) Effects of the drug combination of present invention on mice with sterility induced by androgens 1. Experimental Materials TP (testosterone propionate), the drug combination of present invention, Clomifenecitrate capsules (commercially available), Kunming mice. Gynecological endocrine ELISA kit and instrument, electronic balance, low speed autobalancing centrifuge, etc.

2. Experimental Methods and Results 2.1 Animal Grouping and Model Building

120 Kunming female mice (20 days old) were randomly divided into 6 groups according to their weights and there were 20 in each group. 20 mice in the normal control group were subcutaneously injected with saline and the remaining 100 mice were used in modeling and subcutaneously injected with TP (testosterone propionate). The modeling method is described like this, 100 mice were subcutaneously injected with 0.06 mL TP (testosterone propionate), 4d/time, continuous injection for 2 weeks and drug withdrawal for 1 weeks. Those mice after modelling were randomly divided into three groups, i.e. model control group, Clomifenecitrate capsules group and HDG(high-dose group), MDG (medium-dose group) and LDG (low-dose group) of the drug combination in the present invention.

Experimental animals were fed separately in cages (2 cages in each group) and the experimental conditions include natural illumination, room temperature 17-20° C., humidity 50%-70%, creation of 12-hour illumination & 12-hour dark environment inside the space. Throughout the experiment, the mice were able to consume freely and drink water. Complete pellet feeds were used in feeding and the drinking water was replaced on daily basis.

2.2 Medication for Female Mice

Blank control group: Intragastrically administrated with distilled water on daily basis at a dose of 2 ml/d;

Model control group: Intragastrically administrated with distilled water on daily basis and at a dose of 2 ml/d;

Clomifenecitrate capsules group: Intragastrically administrated with Clomifenecitrate capsules suspension at a dose of 18 mg/kg HDG(high-dose group) of drug combination in the present invention: Intragastrically administrated with the drug combination at a dose of 6 g/kg (calculated as per the crude drug weight);

MDG(medium-dose group) of drug combination in the present invention: Intragastrically administrated with the drug combination at a dose of 4 g/kg;

LDG (low-dose group) of drug combination in the present invention: Intragastrically administrated with the drug combination at a dose of 2 g/kg;

After 4 weeks of administration, the drug was suspended for 48 h, 10 mice were executed in each group and the remaining 10 mice were left to carry out the conception rate test.

3. Experimental Results 3.1 Effect of the Drug Combination in the Present Invention on the Estradiol Content in the Sera of Laboratory Animals.

Irrigation was stopped for 48 h, orbital blood of mice was collected, serum was separated and enzyme linked immunosorbent assay was used to detect E2. The results are recorded as shown in Table 1.

Comparison of E2 content in the mice sera of each group: $\bar{x} \pm s$

| Group category | Number of animals | $E_2/(\text{ug}\cdot L^{-1})$ |
| --- | --- | --- |
| Normal control group | 10 | 9.95 ± 2.43 |
| Model control group | 10 | 5.64 ± 1.65* |
| Clomifenecitrate capsules group | 10 | 12.76 ± 4.98## |
| HDG (high-dose group) of drug combination in the present invention | 10 | 10.59 ± 2.83## |
| MDG (medium-dose group) of drug combination in the present invention | 10 | 7.80 ± 3.95# |
| LDG (low-dose group) of drug combination in the present invention | 10 | 5.72 ± 2.04 |

Note:
comparison with the normal control group, *P < 0.05;
comparison with the model control group, #P < 0.05, ##P < 0.01.

Note: comparison with the normal control group, *P<0.05; comparison with the model control group, #P<0.05, ##P<0.01.

As indicated in Table 1, in the HDG(high-dose group) and MDG(medium-dose group) of drug combination in the present invention, the estrogen level of modeled mice significantly increased if compared with that of the model control group, indicating that the drug combination in the present invention possesses the role of enabling it to be back to normal. Among the rest, the effects of HDG(high-dose group) was close to that of Clomifenecitrate capsules group.

3.2 Effects of the drug combination in the present invention on the quantities of follicles, oocytes, interstitial gland composition and estrogen receptor (ER) among experimental animals.

Mice were executed and their ovaries and uterus were removed. Ovaries were fixed with 100 g formaldehyde and tissue slices were observed under the ordinary optical microscope after the process of HE tinction and oil red 0 tinction.

Uterus were fixed with 100 g/L formaldehyde and tissue slices were imbedded with paraffin and undergone the process of 4 μm slicing and ER marking. Light microscopy was used for observation after the hematoxylin counter staining. IHC was used to detect ER and the record results are as shown in Table 2.

The quantities of follicles, oocytes, interstitial gland composition and comparison of estrogen receptor (ER) expression rate $\bar{x}\pm s$ among mice in every group in Table 2.

| Group category | Number of animals | Quantity of follicles/piece | Quantity of oocytes/piece | Interstitial gland composition | ER expression rate/% |
|---|---|---|---|---|---|
| Normal control group | 10 | 14.6 ± 3.0 | 14.6 ± 3.0 | 27.00 ± 7.90 | 36.64 ± 6.27 |
| Model control group | 10 | 10.3 ± 2.6 | 3.1 ± 1.2** | 42.00 ± 10.02* | 68.00 ± 9.98** |
| Clomifenecitrate capsules group | 10 | 37.6 ± 6.4## | 8.7 ± 2.2# | 24.96 ± 5.00 | 14.25 ± 4.34## |
| HDG (high-dose group) of drug combination in the present invention | 10 | 24.5 ± 4.1## | 6.7 ± 2.5## | 38.52 ± 1.49* | 31.20 ± 4.79## |
| MDG (medium-dose group) of drug combination in the present invention | 10 | 20.9 ± 3.9## | 5.2 ± 2.1## | 34.68 ± 6.99* | 17.21 ± 5.74## |
| LDG (low-dose group) of drug combination in the present invention | 10 | 18.2 ± 2.4# | 4.7 ± 1.9## | 32.76 ± 4.97* | 30.48 ± 4.06## |

Note:
comparison with the normal control group, *P < 0.05, **P < 0.01;
comparison with the model control group, #P < 0.05, ##P < 0.01.

Note: comparison with the normal control group, *P<0.05,**P<0.01; comparison with the model control group, #P<0.05, ##P<0.01.

As indicated in the experimental results, HDG, MDG and LDG of drug combination in the present invention can increase the quantities of follicles and oocytes, develop interstitial glands, promote the follicular development and generate ovulation and corpus *luteum*. The effect of modeling on interstitial substance was not obvious and Clomifenecitrate capsules group had insignificant effect on the interstitial gland after medication. Among the experimental animals in HDG, MDG and LDG of drug combination in the present invention, the levels of interstitial glands after medication were higher than that of the normal control group, explaining indirectly that the drug combination in the present invention exert their efficacies by regulating the overall function of reproductive organs, rather than only stimulating ovarian follicles.

3.3 Conception Conditions of Mated Female Mice after the Medication.

To put 10 mice from each cage into the cage where 4 normally-matured male mice. 10 d after the mating, uterus of female mice were dissected to observe the conception conditions. The record results are as shown in Table 3.

TABLE 3

Conception conditions of mated female mice after the medication.

| Group category | Number of animals | Number of conception/mice | Rate of conception % |
|---|---|---|---|
| Normal control group | 10 | 6 | 60.0 |
| Model control group | 10 | 2 | 20.0 |
| Clomifenecitrate capsules group | 10 | 6 | 60.0 |
| HDG (high-dose group) of drug combination in the present invention | 10 | 5 | 50.0 |
| MDG (medium-dose group) of drug combination in the present invention | 10 | 5 | 50.0 |
| LDG (low-dose group) of drug combination in the present invention | 10 | 3 | 30.0 |

For the HDG and LDG of drug combination of the present invention, the PR(pregnancy rate) was slightly lower than that of Clomifene citrate capsules group and normal control group, indicating that the HDG and LDG of drug combination can effectively restore the physiological functions of modelled experimental animals.

(2) Effects of the Drug Combination of Present Invention on Mice with Fallopian Tube Inflammatory Obstructive Infertility 72 wistar female rats were randomly divided into 6 groups according to their weights and there were 12 rats in each group. Except for 12 rats in the blank control group, the remaining 60 rats were put into the modelling experiment aimed to induce the fallopian tube inflammatory obstructive infertility. Rats in the modelling group were fasted for 24 h (food was forbidden, drinking permitted), 20% urethane (5 ml·kg$^{-1}$) was used in anaesthesia, ventral hair was cut away to open the abdominal cavity after iodine and alcohol disinfection. Next, 4# scalp needle was used to inject 20% phenol paste of 0.01 ml into ovarian ducts on both sides at the uterine bifurcation and sutured the wound. After the operation, 5 groups were randomly divided and there were 12 rats in each group, i.e. model control group (equal volume of distilled water was given), Fuyankang tablets group (0.41 g·kg$^{-1}$), as well as HDG, MDG and LDG of the drug combination of the present invention. 30 d after respectively continuous intragastric administration, pharmacodynamic hemorheology detection was conducted by drawing blood and uterus was also taken for observation by naked eye. The record results are as shown in Table 4 and Table 5.

TABLE 4

Comparison of fallopian tube patency in modelled rats

| Group category | Number of animals | Number of fallopian tube | Number of patency | Number of blockage | Patency rate (%) |
| --- | --- | --- | --- | --- | --- |
| Normal control group | 12 | 24 | 24 | 0 | 100 |
| Model control group | 12 | 24 | 4 | 20 | 16.67 |
| Fuyankang tablets group | 12 | 24 | 14 | 10 | 58.33## |
| HDG (high-dose group) of drug combination in the present invention | 12 | 24 | 11 | 13 | 45.83## |
| MDG (medium-dose group) of drug combination in the present invention | 12 | 24 | 8 | 16 | 33.33## |
| LDG (low-dose group) of drug combination in the present invention | 12 | 24 | 5 | 19 | 20.83# |

Note:
comparison with the model control group, #P < 0.05, ##P < 0.01;

Note: comparison with the model control group, #P<0.05, ## P<0.01;

The tubal patency rate of rats in the model group was 16.67% and the number of blockage was obviously higher than that of the normal control group, indicating that the injection of 20% 0.01 mL phenol paste into the ovarian duct may lead to obstruction due to ureteritis. In HDG, MDG and LDG of the drug combination of the present invention, the tubal patency rate of rats was higher than that of Fuyankang tablets group. For this reason, the drug combination in the present invention can improve the symptoms of fallopian tube obstruction.

TABLE 5

Effects of the drug combination in the present invention on the hemorheology in rats

| Group category | Number of animals | High cut | Low cut | PV (plasma viscosity) |
| --- | --- | --- | --- | --- |
| Normal control group | 12 | 2.33 ± 0.35 | 9.85 ± 2.25 | 2.37 ± 0.82 |
| Model control group | 12 | 3.28 ± 1.02 | 16.03 ± 3.67 | 3.56 ± 0.68 |
| Fuyankang tablets group | 12 | 2.58 ± 0.69* | 13.49 ± 3.62* | 2.79 ± 0.75 |
| HDG (high-dose group) of drug combination in the present invention | 12 | 2.49 ± 0.92* | 10.94 ± 2.63** | 2.43 ± 0.52* |
| MDG (medium-dose group) of drug combination in the present invention | 12 | 2.53 ± 0.97* | 12.23 ± 2.74* | 2.72 ± 0.69 |
| LDG (low-dose group) of drug combination in the present invention | 12 | 3.57 ± 1.20 | 14.92 ± 3.18 | 3.38 ± 1.14 |

Note:
comparison with the model control group, *P < 0.05, #**P < 0.01;

Note: comparison with the model control group, *P<0.05, #**P<0.01;

The high cut, low cut and PV (plasma viscosity) of model group rose if compared with the normal control group, indicating that abnormal hemorheologic indexes occurred in rats with obstruction due to ureteritis. In HDG, MDG and LDG of the drug combination of the present invention, the whole blood viscosities (low & high cut) of rats significantly decreased if compared with that of the model group and no obvious difference if compared with Fuyankang tablets group. For the HDG group, the difference was significant if compared with the model group. It is quite evident that the drug combination in the present invention has reducing effect on the whole blood viscosities (low & high cut) and PV (plasma viscosity) of 20% rats with fallopian tube inflammatory obstructive infertility caused by phenol paste.

Testing Example 2 a Study on the Effects of Anti-Fatigue and Hypoxia Tolerance Efficacy Test materials, drugs and animals were the same as that in testing example 1.

160 healthy Kunming mice (weights 22±2 g) were randomly divided into 8 groups and each of two groups was taken as an experimental group. I group was the control group and intragastric administration of equivalent normal saline was arranged. For II-IV groups, the intragastric administration of drug combination in the present invention was arranged as per three dosages, i.e. 6(HDG), 4 (MDG) and 2 (LDG)g/kg, 1 time/d and constant administration for 7 d. 30 min after the end of last administration, a group of mice were tied with load equivalent to 5% of the mice weight. Next, these mice were put into a glass jar. Physical exhaustion was considered when the head of mice was plunged into the water for 10 s and failed to come to the surface. In this case, the time from the commencement of swimming to the physical exhaustion was recorded as the load swimming time of mice. Another group of mice were put into a 500 mL ground mouth &wide-mouth bottle filled with 15 g soda lime (1 bottle for each mouse). Next, Vaseline was used to seal the bottle neck and started the timing. Stop watch was used to record the time from the hermetization of bottle neck to the death time of mice, which was recorded as the hypoxia time of mice.

TABLE 6

Effects of oral administration of the drug combination on the mice activity

| Group category | Number of mice (piece) | Administration dosage (g/kg) | Load swimming time (min) | Hypoxia time (min) |
|---|---|---|---|---|
| Normal control group | 20 | — | 8.40 ± 1.25 | 81.25 ± 23.58 |
| HDG (high-dose group) of drug combination in the present invention | 20 | 6 | 12.23 ± 3.40 | 106.30 ± 21.57 |
| MDG (medium-dose group) of drug combination in the present invention | 20 | 4 | 11.54 ± 1.62 | 97.26 ± 18.35 |
| LDG (low-dose group) of drug combination in the present invention | 20 | 2 | 10.02 ± 1.14 | 90.49 ± 15.94 |

In the HDG, MDG and LDG of drug combination of the present invention, the load swimming time and hypoxia time of mice were higher than that of the normal control group, indicating that the drug combination in the present invention can improve the mice activity and strengthen the physique of mice.

Testing Example 3 Effects of the Drug Combination in the Present Invention on the Immune Function of Mice Test materials, drugs and animals were the same as that in testing example 1.

140 SPF-grade Kunming male mice (body weights 18-22 g) were taken and divided into 7 groups and there were 20 mice in each group. Except that 20 mice in the blank control group were given equivalent normal saline, the remaining mice administrated with the drug combination (HDG, MDG and LDG) of the present invention. The intragastric administration was conducted on daily basis with a dose of 20 ml/kg every day, 1 time for 1 d and continue for 30 d. After these mice were executed, the following tests were conducted: (1) ConA-induced mouse spleen lymphocyte transformation test (MTT method); (2) Determination of numbers of antibody-producing cells (modified Jerne's method); (3) Determination of serum hemolysin (blood agglutination test); (4) Mouse abdominal cavity macrophage swallows the chicken red blood cell experiment (semi-in-vivo method). The record results are as shown in Table 7 and Table 8.

TABLE 7

Effects of the drug combination in the present invention on ConA-induced mouse spleen lymphocyte transformation ability, the number of antibody-producing cells, serum hemolysin ($\bar{x} \pm s$, n = 20)

| Group category | Dosage/ (g/kg) | Lymphocytes proliferation assay [D($\lambda$)] | Number of hemolysis plaque (1 × $10/10^8$ number of splenocyte) | Antibody volume |
|---|---|---|---|---|
| Blank control group | — | 0.2439 ± 0.0613 | 182.4 ± 20.3 | 120.3 ± 16.4 |
| HDG (high-dose group) of drug combination in the present invention | 6 | 0.3367 ± 0.0635* | 212.7 ± 16.9** | 149.7 ± 14.9* |
| MDG (medium-dose group) of drug combination in the present invention | 4 | 0.3148 ± 0.0597 | 199.2 ± 14.5 | 134.5 ± 13.3 |
| LDG (low-dose group) of drug combination in the present invention | 2 | 0.2871 ± 0.0840 | 192.8 ± 13.0 | 129.8 ± 13.7 |

Note:
comparison with the blank control group, *$P < 0.05$, **$P < 0.010$;

Note: comparison with the blank control group, *P<0.05, **P<0.010;

As indicated in Table 7, if compared with the blank control group, the HDG, MDG and LDG of drug combination in the present invention increased in terms of lymphocyte proliferation ability, hemolytic plaque number and antibody volume, indicating that drug combination in the present invention can promote the lymphocyte proliferation and transformation ability in mice, enhance the antibody-producing cell proliferation in mice and increase the level of serum hemolysin in mice.

TABLE 8

Effects of the drug combination in the present invention on mouse abdominal cavity macrophage swallows the chicken red blood cell ($\bar{x} \pm s$, n = 20)

| Group category | Dosage/ (g/kg) | Phagocytic rate/% | Pyagocytic index |
|---|---|---|---|
| Blank control group | — | 24.3 ± 4.6 | 0.497 ± 0.098 |
| HDG (high-dose group) of drug combination in the present invention | 6 | 31.7 ± 4.9 | 0.763 ± 0.182* |
| MDG (medium-dose group) of drug combination in the present invention | 4 | 27.5 ± 4.3 | 0.628 ± 0.131 |
| LDG (low-dose group) of drug combination in the present invention | 2 | 25.9 ± 4.0 | 0.512 ± 0.125 |

Note:
comparison with the blank control group, *P < 0.05.

Note: comparison with the blank control group, *P<0.05.

As indicated in Table 8, the phagocytic indexes of HDG, MDG and LDG in the drug combination in the present invention were significantly higher than that of blank control group, indicating that it plays a certain role of promoting the phagocytic function of mice's peritoneal macrophage.

Testing Example 4 Safety Evaluation

Test materials, drugs and animals were the same as that in testing example 1.

1. Acute Toxicity Test

The mice were intragastrically-administered with 50 g (crude drug)/kg of test preparation and no animal deaths were found during the testing period. In this case, it can be determined that the maximum tolerance dose for single dosage was 50 g (crude drug)/kg, which was equivalent to 125 times as high as the daily consumption of humankind (calculated as per the weight of 60 kg/each person, dosage of capsule: 2 capsules at each time, one time every day, 12 g of crude drug is contained in each capsule, daily consumption per person is 24 g, 0.4 g/kg/day).

2. Long-Term Toxicity Test

Continuous intragastric administration at a dosage of 20 g/kg were provided to rats for 10 weeks and there were no toxicity changes in terms of general clinical symptoms, weight gain, indicators of hematology and blood biochemistry examination, related organ systems and pathological tissues among animals, if compared with the distilled water in control group. 4 weeks after the suspension of drug, delayed toxicity was not found in the examination of the above same items, indicating that the oral successive medication of the drug combination in the present invention have no obvious toxic side effects.

In summary, the compatibility of this drug combination invented is precise, appropriate and possess outstanding curative effects. As shown in many experiments, the drug combination invented is safe and reliable, its toxic & side-effect is low and it has obvious improvement effects on female infertility caused by androgen, fallopian tube inflammation, tubal blockage and other factors. Furthermore, it can not only significantly improve the success rate of pregnancy, but also improve immunity and enhance the body's anti-fatigue and hypoxia tolerance. In short, the invention provides a safe and reliable new choice for clinical medication.

What is claimed is:

1. A method of treating infertility in a subject suffering therefrom, comprising administrating to the subject a pharmaceutically effective dosage of a composition which is prepared by the following steps:
    (1) obtaining 80 g dried *Nelumbo nucifera* leaves and cutting said leaves into pieces and extracting with 500 ml distilled water at 4° C. for 12 hours; then
    (2) filtering through a Whatman paper No. 1; and
    (3) concentrating by evaporation; and
    (4) lyophilizing to yield *Nelumbo nucifera* leaves extract (NLE); then
    (5) adding NLE to a plurality of crude drugs and then add a solvent, and then extracting to produce said composition;
    wherein a crude drug is defined as a plant material prior to extraction; and
    wherein the plurality of crude drugs include:
    15 kg of Rehmannia, 15 kg of Chinese Peony, 15 kg of Asiatic Dogwood, 15 kg of Chinese Yam, 15 kg of Poria, 20 kg of *Astragalus,* 20 kg of Codonopsis, 15 kg of Epimedium, 15 kg of Jujube, and 60 kg of *Acacia* extracts.

* * * * *